US006328928B1

(12) United States Patent
Schroeder et al.

(10) Patent No.: US 6,328,928 B1

(45) Date of Patent: Dec. 11, 2001

(54) METHOD AND FOR PREPARING CONTAINER FOR FILLING, AND METHOD OF FILLING CONTAINER

(75) Inventors: Klaus Schroeder; Ulrich Steinhauser, both of Ahaus (DE)

(73) Assignee: GEA Finnah GmbH, Ahaus (DE)

(*) Notice: Subject to any disclaimer, the term of this patent is extended or adjusted under 35 U.S.C. 154(b) by 0 days.

(21) Appl. No.: 09/254,296

(22) Filed: Mar. 3, 1999

(30) Foreign Application Priority Data

Jan. 7, 1997 (DE) ............................................. 197 00 156

(51) Int. Cl.[7] ................................ A61L 2/00; A61L 9/00

(52) U.S. Cl. ................................ 422/28; 134/18; 134/61; 134/72; 422/1; 422/26; 422/292; 422/297; 422/300; 422/302; 422/303

(58) Field of Search ..................................... 422/292, 297, 422/300, 302, 303, 28, 1, 26; 134/18, 61, 72

(56) References Cited

U.S. PATENT DOCUMENTS 3,531,299 * 9/1970 Benjamins ........................... 422/303
3,575,713 * 4/1971 Duff et al. ........................... 422/302
4,296,068 * 10/1981 Hoshino ................................ 422/62
4,680,163 * 7/1987 Blindschun et al. ................... 422/28
4,707,334 * 11/1987 Gerhard ................................ 422/28
4,742,667 * 5/1988 Muller et al. .......................... 53/167
4,900,527 * 2/1990 Lierke ................................. 422/302
4,934,392 * 6/1990 Henfrey ................................ 134/60
5,792,435 * 8/1998 Mueller et al. ....................... 422/292

FOREIGN PATENT DOCUMENTS 3701915 8/1988 (DE) .

* cited by examiner

*Primary Examiner*—Krisanne Thornton

(74) *Attorney, Agent, or Firm*—Jordan and Hamburg LLP

(57) ABSTRACT

A method and a machine for preparing and filling containers with a product, for which method and machine the containers are grouped in rows at right angles to the transporting direction with the container openings facing upwardly and aligned at a distance from one another. The containers are swiveled, row by row, into an at least approximately vertical position with the container openings facing downwardly and rinsed jointly on the inside with a cleansing agent. The rinsed containers are dried on the inside in a first drying station and, after passing through the first drying station, are charged into a sterile environment. After a row of containers has entered the sterile environment, the containers are sterilized on the inside by means of a sterilizing agent and, in a second drying station, residues of sterilizing agent are expelled from the sterilized containers. In the event that the containers are to be filled with a carbon dioxide-containing and/or a nitrogen-containing material, the containers are wetted subsequently on the inside with sterile water and, after being dried, are swiveled in a second turning process into a filling position with the container openings facing upwardly. The containers subsequently are filled with the specified amount of product and, in a sealing station, sealed at least provisionally with a stopper part, after which the sealed containers are discharged from the sterile region.

34 Claims, 7 Drawing Sheets

68

67
66
69
11
64
65
63
63
62

METHOD AND FOR PREPARING CONTAINER FOR FILLING, AND METHOD OF FILLING CONTAINER

BACKGROUND OF THE INVENTION

The invention relates to a method and to a machine for preparing containers for being filled and for filling containers, especially polyester containers, with a material forming a beverage.

In order to ensure their keeping qualities, numerous beverages have to be filled under special conditions, which are described by the concepts of "clean", "ultraclean" or "aseptic" and contain certain germ count limits ($10^{-4}$, $10^{-6}$). To ensure the respective conditions, it is customary, for example, to fill the material at an elevated temperature, such as 92° C. The sterilization of bottles and the filling of sterilized bottles in a sterile environment is also known (DE 37 01 915 A1), the bottles initially being heated to a relatively high temperature by infrared radiators and subsequently cooled before the filling process. Such methods can be used for glass bottles and thick-walled plastic bottles, but not for thin-walled polyester bottles, which offer only a slight dimensional stability and may not be heated to a temperature above 45° C., if they are not to experience loss of dimensional stability.

SUMMARY OF THE INVENTION

The invention is concerned with the problem of providing a method and a machine, which enable thin-walled polyester bottles to be filled at a high efficiency under aseptic conditions.

The inventive method and the inventive machine group the bottles in transverse rows. A larger number of bottles, such as nine bottles, can be subjected simultaneously in a transverse row to the treatment processes. The turning of the bottles into a position, in which the opening points downward, makes possible the simple, effective and rapid cleaning and drying, sterilization with a sterilizing agent suitable for the purpose, as well as a subsequent expulsion of the residues of the sterilizing agent and finally, if necessary, also a wetting of the bottles with sterile water in the event that the bottles are to be filled with a beverage containing carbon dioxide or nitrogen. After the bottles are turned once more, they can then be filled with the intended material. During their sterilization and until they are sealed after being filled, the bottles are in an aseptic environment so that, despite the fact that the temperature in the bottle material has dropped below the load limit temperature of 45° C., it is assured that, in all processing stations, the beverages, filled into the bottles, have the required keeping qualities of, usually, about six months.

Further details and advantages arise out of the following description and the drawing, in which an example of the object of the invention is illustrated diagrammatically in greater detail.

DESCRIPTION OF THE PREFERRED EMBODIMENTS

Figure 1:
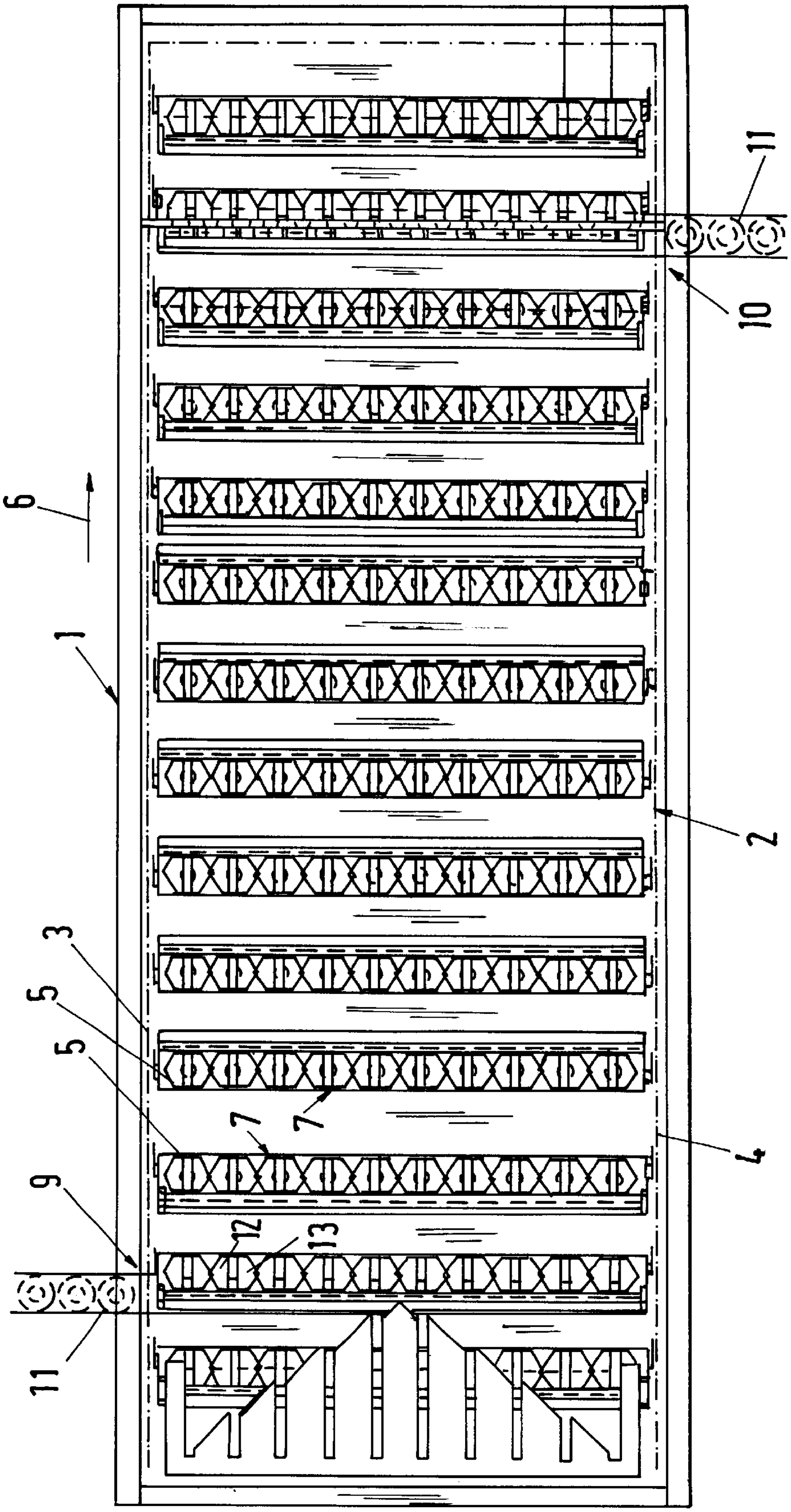
FIG. 1 shows a diagrammatic plan view of the conveying equipment of the inventive machine.
Figure 2:
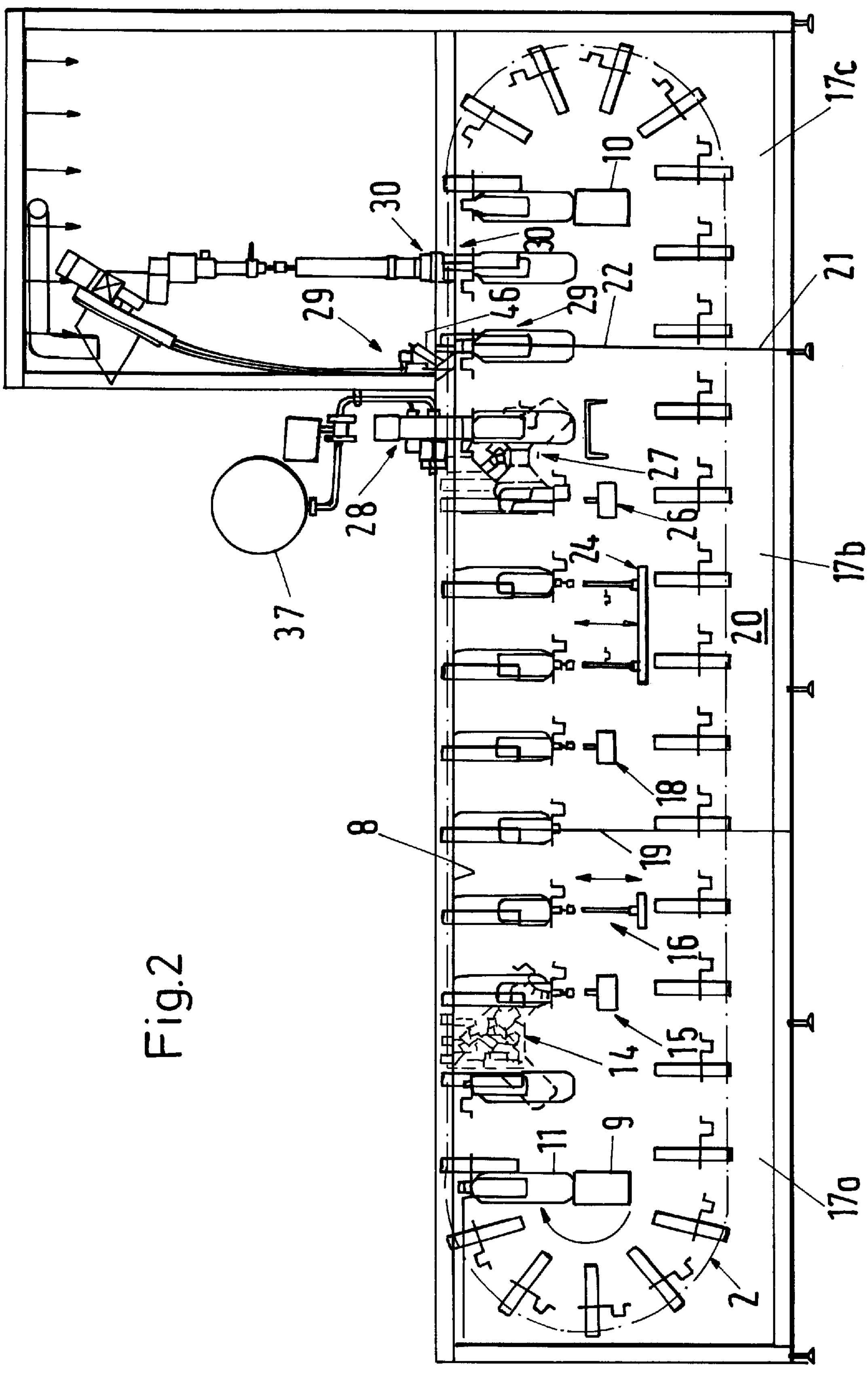
FIG. 2 shows a diagrammatic side view corresponding to FIG. 1.

As shown in FIGS. 1 and 2, the inventive machine comprises a machine frame 1, which supports conveying equipment 2. The conveying equipment 2 is constructed as an endless chain conveyor and comprises bottle carriers 5, which can be swiveled relative to the conveying chains 3, 4 on the outside and locked in two different swiveling positions and which in each case have a number of bottle holders 7, disposed next to one another transversely to the transporting direction 6. The bottle carriers 5 form a modular unit, which extends transversely essentially over the width of the conveying equipment 2, and are supported consecutively at the conveying chains 3, 4 at mutually identical distances.

With the help of the conveying equipment 2, the bottles, which are to be filled, are transported along a straight conveying path, which is defined by a guide 8 of the machine frame 1, through the machine from a loading station 9 to a discharging station 10, the bottles 11 being grouped in rows transversely to the transporting direction 6 and aligned at a distance from one another independently of their diameter and centered, and moreover with the help of self-aligning gripper parts 12, 13 of the bottle holders 7.

Downstream from the loading station 9 in the transporting direction 6, diagrammatically indicated turning equipment 14 (FIG. 2) is disposed, in which the bottles 11, supplied to the loading station 9 with upwardly pointing bottle openings and taken over in this position by the bottle holders 7, are swiveled transverse row by transverse row into a vertical position with downwardly pointing bottle openings, this being done by swiveling in each case a whole bottle carrier 5 relative to the conveying chain 3, 4 supporting this bottle carrier 5.

The transverse rows of bottles, transported discontinuously, initially pass through spray equipment 15 for, at the same time, introducing cleansing agent in an upwardly directed jet into the interior of the bottles 11 of a transverse row. By these means, the bottles 11 are rinsed on the inside and any particles, such as dust particles or the like, contained in them are cleaned out. As cleansing agent, preferably sterile water is used, which is under a pressure ranging from 2 to 4 bar and preferably of 4 bar and has a temperature ranging from 40° to 50° C. and preferably of about 45° C.

The cleaned bottles 11 next pass through first drying equipment 16, by means of which residues of cleansing agent, remaining in the interior of the bottles 11, are expelled simultaneously from all bottles 11 of the transverse row located in the drying station. As drying agent, preferably heated, sterile, compressed air is used, which is blown into the interior of the bottles and is under a pressure of about 2 to 4 bar and preferably of 3 bar and has a temperature ranging from about 40° to 90° C. and preferably of about 60° C. Even if the temperature of the compressed air is higher than the load limit temperature for the material of the bottles 11, then this does not lead to any thermal impairment of the bottles 11 since, given the brevity of the action of the compressed air, the walls of the bottles 11 do not reach temperatures, which exceed the load limit.

Figure 3:
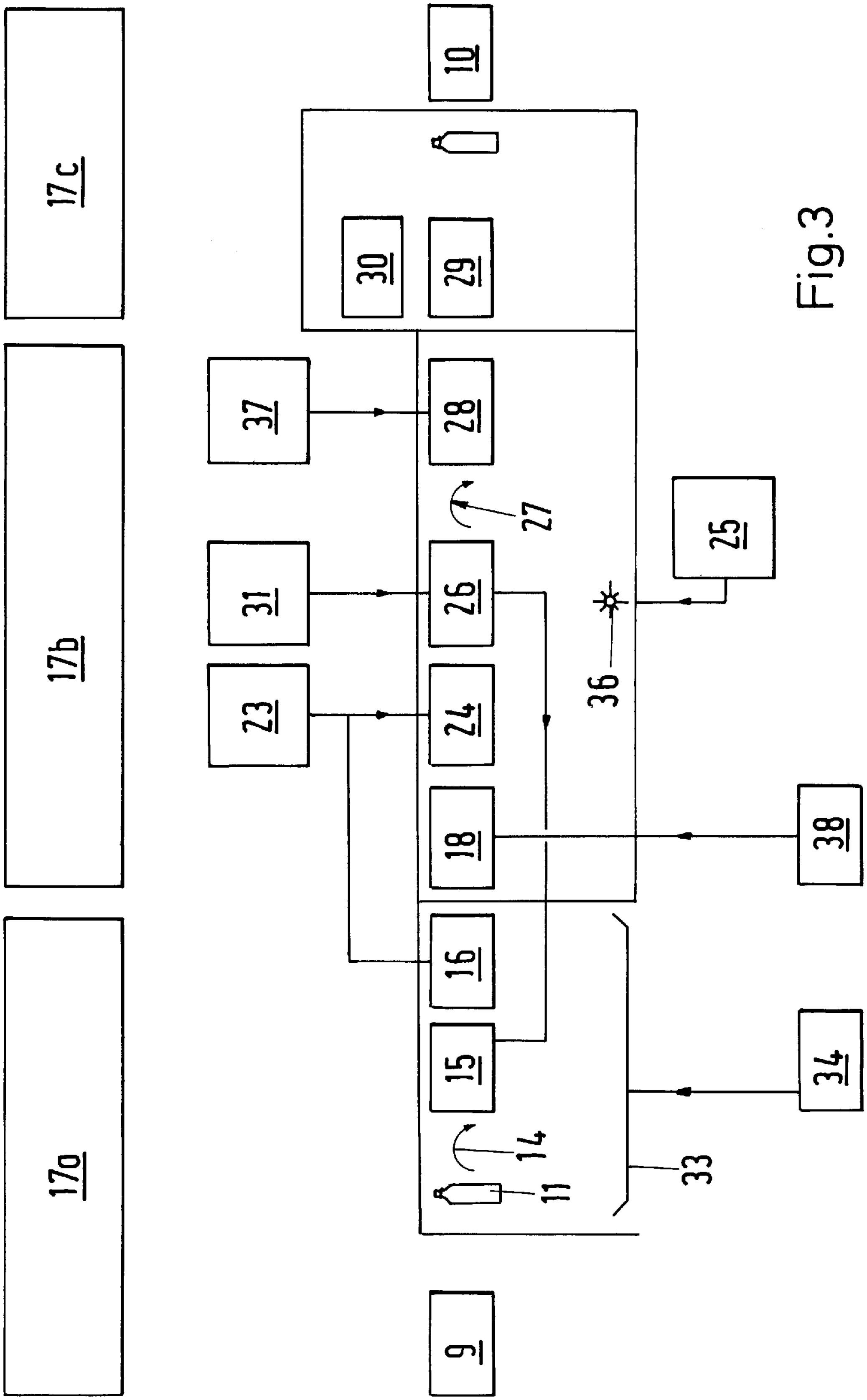
FIG. 3 shows a flow diagram of the handling and processing processes.

Up to the first drying station 16, the bottles 11 are in a non-sterile input and washing area 17*a* (FIG. 3). Upon further transport to spray equipment 18 forming a sterilization station, the row of bottles, leaving the drying station, passes through a charging opening 19 into a closed interior space 20 of a housing 21, in which there is a sterile atmosphere. This is formed by sterile air, which is blown into the interior space 20, takes up all of the space and flows out of the charging opening 19 and a discharging opening 22 to the outside, in order to prevent the entry of germ-laden air. The sterile air is supplied by a source 23 of sterile air, to which the tunnel-like housing 21, defining a sterile region 17*b*, is also connected. The tunnel-like housing 21 can, however, also be acted upon by sterile air from an independent source From the spraying equipment 18, the interior of the bottles 11 in a row is acted upon simultaneously by a sterilizing agent, which is introduced into the interior of the bottles with an upwardly directed jet. As sterilizing agent, preferably hydrogen peroxide ($H_2O_2$) is used. However, any other sterilizing agent, in liquid or vapor form, sterilizing by chemical and/or physical means, can be used. In pressure and temperature, the sterilizing agent can correspond to the cleansing agent.

After the sterilization, the bottles 11 reach a second drying station 24, in which residues of sterilizing agent are expelled from the interior of the bottles 11 in much the same way as in the first drying station 16 with the help of heated sterile air. The sterile air for the second drying station 24, like that for the first drying station 16, originates from the sterile air source 23. The pressure can be between 2 and 4 bar and preferably is about 3 bar, and the temperature of the compressed air for the second drying equipment 24 is between 40° and 90° C. and preferably is about 60° C.

Upon leaving the second drying station formed by the second drying equipment 24, the bottles 11 reach a wetting station 26 which, however, is required or operated only if the bottles 11 are to be filled with a material containing carbon dioxide or nitrogen. In the wetting station formed by the wetting equipment 26, the interiors of all the bottles 11 in a transverse row are wetted simultaneously with sterile water, the equipment, similar to the equipment 15 or 16, being constructed as spraying equipment, which delivers the sterile water into the interior of the bottles from below with an upwardly directed jet.

Upon leaving the wetting equipment 26, the bottles 11 reach the second turning equipment 27, in which they are turned once again and, after that, aligned at least approximately vertically with the opening of the bottles directed upwards. In this position, the bottles are filled with the liquid material, preferably soft drinks and, moreover, row by row simultaneously by means of filling equipment 28.

When filled, the bottles 11 reach the first sealing equipment 29, in which the bottle openings are supplied with a stopper part (not shown). The stopper part may, for example, be a screw cap, as used for screw type closures of different kinds. It can also form a provisional seal and the final seal can then be formed by screwing on the cap in the subsequent second sealing equipment 30. However, the stopper part can also be put in place and the bottle finally sealed already in the first sealing equipment, in which case the second sealing equipment 30 can be omitted.

In the region of the first sealing equipment 29, the bottles 11 leave the interior 20 of the housing 21 forming the sterile region 17*b*, passing through the discharging opening 22. At this time, the aseptic filling is concluded and contamination of the bottle contents with microorganisms is precluded. Even after leaving the sterile region 17*b*, the bottles 11, until they reach the discharging station 10, are in a clean region 17*c*, before they are then supplied over the discharging station 10 to optional further processing stations, such as labeling or printing stations, a packing station, etc.

Figure 4:
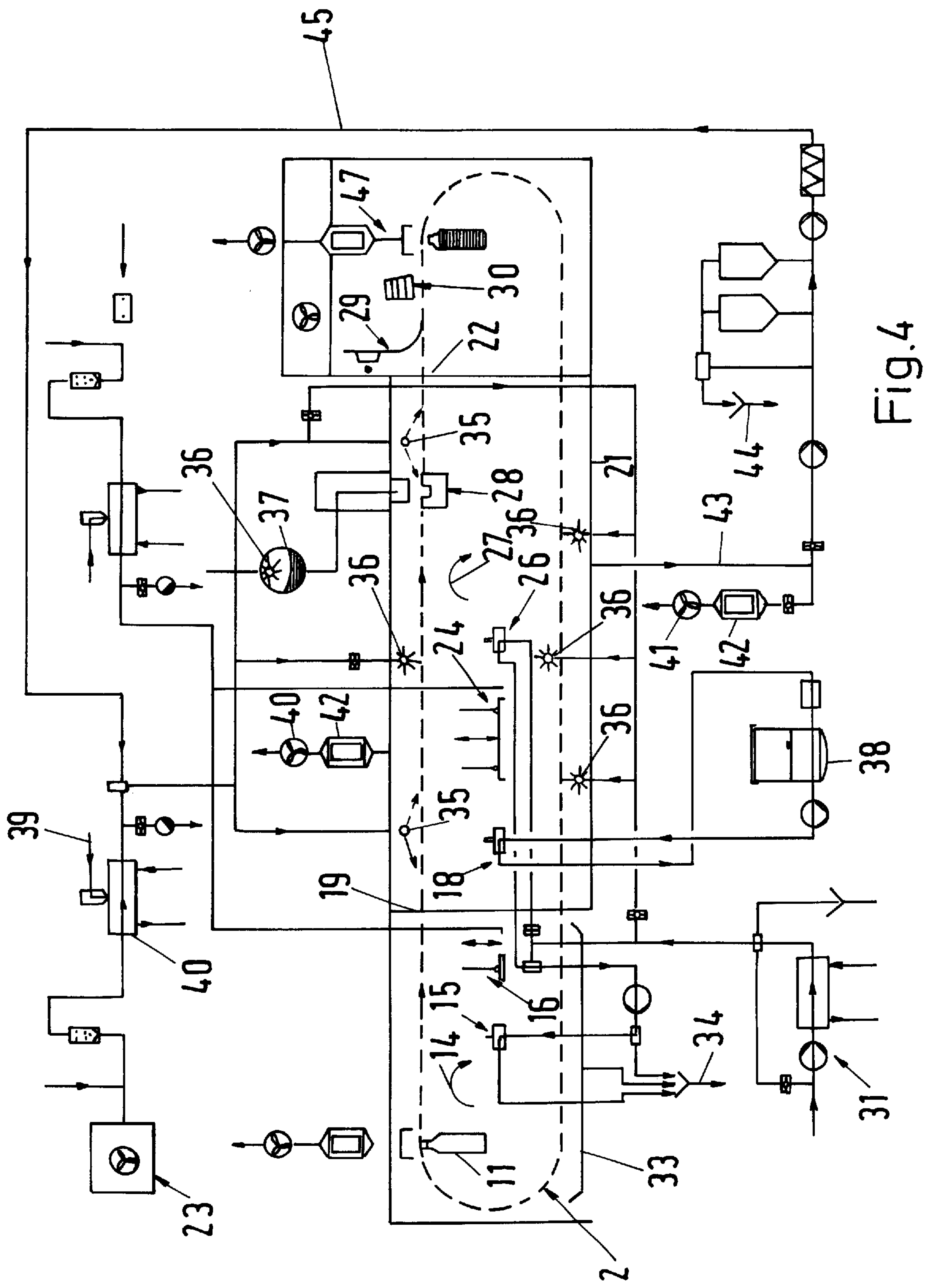
FIG. 4 shows a diagrammatic representation, similar to the flow diagram of FIG. 3, of the processing and treatment units of the inventive machine.

As can be inferred particularly from FIGS. 3 and 4, the cleaning equipment 15 and the wetting equipment 26 preferably are acted upon with sterile water, which originates from the same source 31 and is formed from sterile condensate, the cleansing agent that drains being collected by a bottom part 33 and transferred by this to a collector 34 or to a drain. The source 31 of sterile water can also supply the spray heads 35, 36 of the sterile region 17*b* of the machine with sterile water when CIP cleaning processes are carried out. However, while the production is running, the spray heads 35 serve to blow sterile air into the interior 20 of the housing 21, in order to form and maintain the sterile pressurized atmosphere. Likewise, the spray heads 36 can also be connected to the source 23 of sterile air.

The material, which is to be filled into the bottles, is supplied from a reservoir 37, which can also be subjected to CIP cleaning as is symbolized by the indicated spray head 36.

The spray equipment 18 for introducing sterilizing agent is supplied from a source 38 of sterilizing agent, from which an inlet pipe 39 can also be supplied, which discharges into the sterile air pipe 39 in the region of a heat exchanger 40 for heating the sterile air supplied by the source 23 and makes it possible to treat the sterile air with sterilizing agent. If the sterile air, introduced into the interior space 20 during a production process or during a CIP cleaning process, is treated with sterilizing agent, sterile air, enriched with sterilizing agent, can be withdrawn over the blowers 40, 41, upstream of which in each case a catalyst 42 is disposed for separation purposes.

Over a drainpipe 43, sterile water is supplied to a collector 44 or to a drain corresponding to the collector 34. However, sterile water can also be taken from and supplied to the interior space 20 in a cycling system, as can be seen from the circulation pipe 45 (FIG. 4).

Sterile air, in the form of a laminar curtain, also flows through the clean region 17*c* adjoining the housing 21 in the transporting direction 6, into which housing 21 the conveying equipment 2 enters once again on its way back for sterilizing purposes, so that microorganisms are carried over into the clean region 17*c* only by caps, which have not been sterilized. In order to prevent the possibility of microorganisms in the cap region facing the bottle opening gaining access to the bottles 11 and to the material contained therein, the caps can either be sterilized as a whole before they enter the clean region 17*c* (in which case the sealing equipment 29 and also 30 can be disposed in the sterile region 17*b*) or, before they are put in place on the bottles, sterilized only in the bottle-ready region by being sprayed with hot steam, a sterilizing aerosol, etc. with the help of a spray nozzle indicated at 46. The second sealing equipment 30 can follow exhaust equipment 47, the function of which is to suck off residues of sterilizing agent adhering on the outside to the stopper part and at the neck of the bottle if, for example, sterile air, enriched with sterilizing agent, is also used in the clean region 17*c*.

Figure 5:
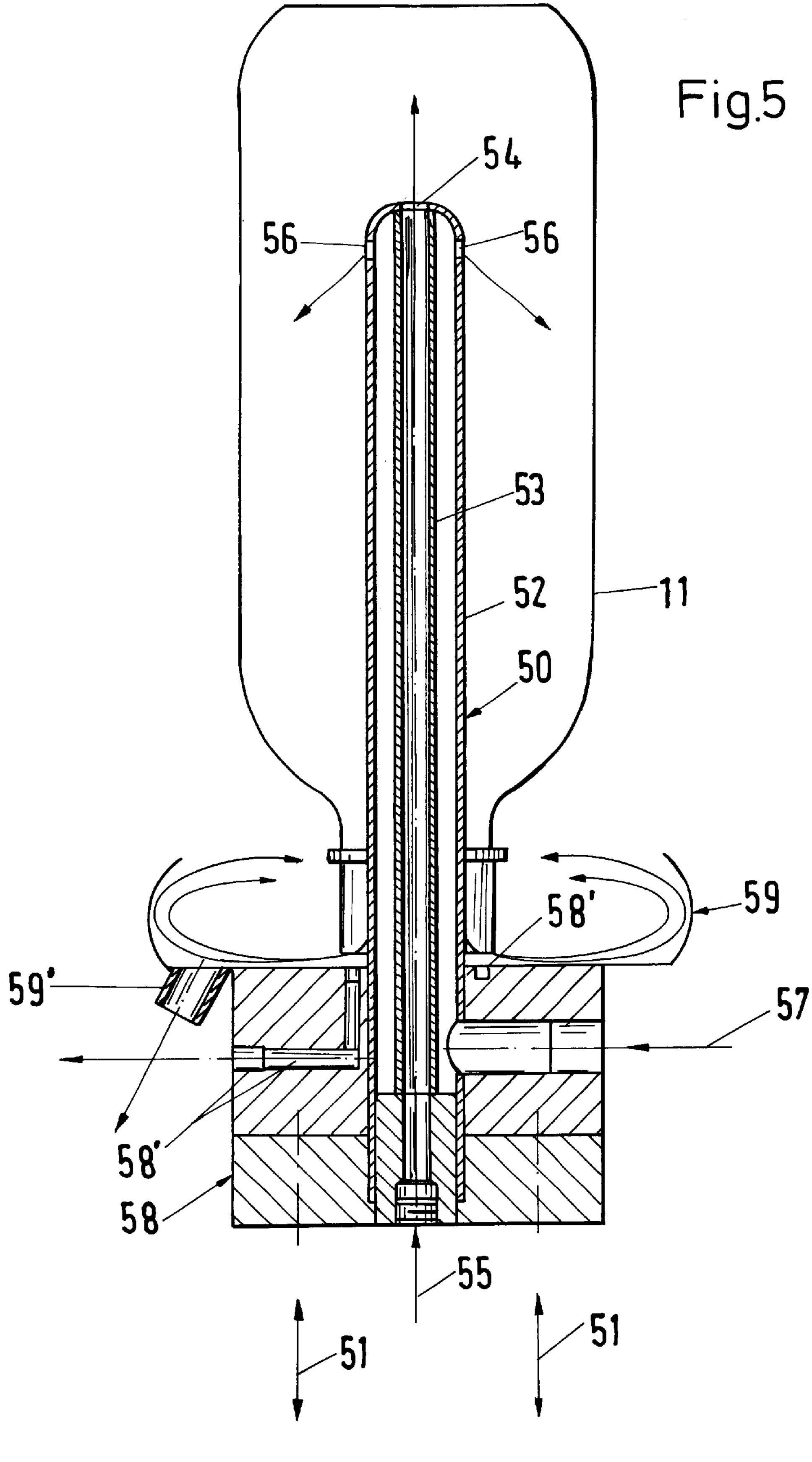
FIG. 5 shows a diagrammatic cross section through a blast lance.

The drying equipment 16, 24 for expelling residues of cleansing agent and sterilizing agent from the interior of the bottles 11 comprise a number of blast lances 50, which corresponds to the number of bottles in a transverse row. The blast lances 50 can be introduced simultaneously in each case from below into the bottles of a transverse row assigned above and moved out of these once again. This is illustrated in FIG. 5 by the arrows 51.

The blast lances 50 comprise, in detail, an outer pipe 52 and an inner pipe 53, which are disposed concentrically to one another and connected with each other at the front end of the blast lance 50. In the front end of the blast lance 50, a first outlet opening 54 for a drying medium is provided which, through the inner pipe 53, is supplied with drying medium, which is supplied over a separate feed pipe 55 to the inner pipe 53. Close to their front ends, the blast lances have second outlet openings 56 at their periphery. These second outlet openings 56 are connected to a separate second feed pipe 57, from which they are supplied over the annular space between the pipes 52, 53 with drying medium.

In operation, the blast lances 50, together with carrier part 58, are shifted from a position, in which the front ends are below the bottle openings, into an upper end position, in which the front ends of the blast lances 50 are close to the bottom of the bottles. As soon as this position is reached, the drying medium is blown out through the outlet openings 54 and, by these means, the region of the bottles 11, close to the bottom, is freed from residues of cleansing agent or sterilizing agent. After that, the blowing out of drying medium through the outlet openings 54 is ended and the drying medium is blown out through the outlet openings 56, which impose an outward and inclined downward direction to the flow of the drying medium, so that, when the downwards motion of the blast lances 50 commences, a strong expulsion effect is exerted on the liquid residues, which are still present in the region of the bottles 11 remote from the bottom.

The blast lances 50 are provided in their base region with a guiding organ 59, which is disposed above their carrier part 58. The guide organ 59 imposes a flow directed back to the neck of the bottle, to the drying medium emerging from the bottle opening. In this way, the outer region of the neck of the bottle is also subjected to cleaning or sterilization by the entrained residues of cleansing agent and sterilizing agent.

In order to support the expulsion effect of the drying medium emerging from the outlet openings 54, 56 of the blast lances 50, a groove 58', which surrounds the base of each blast lance 50 and can be connected over a suction duct 58" to a source of vacuum, is formed in the upper side of the carrier part 58. This improves and accelerates the flow of drying medium out of the bottle opening, which has been narrowed by the blast lance 50. The expelled liquid residues, which otherwise can also be drawn off over the outlet 59' at the guiding organs 59, can also be sucked off over this suction.

As soon as the blast lance 50 has ended its downwards motion, the expulsion of blast air through the outlet openings 56 is also ended. This is undertaken by valves, the details of which are not illustrated and which are disposed in the feed pipes 55, 57 and can be actuated independently of one another.

Figure 6:
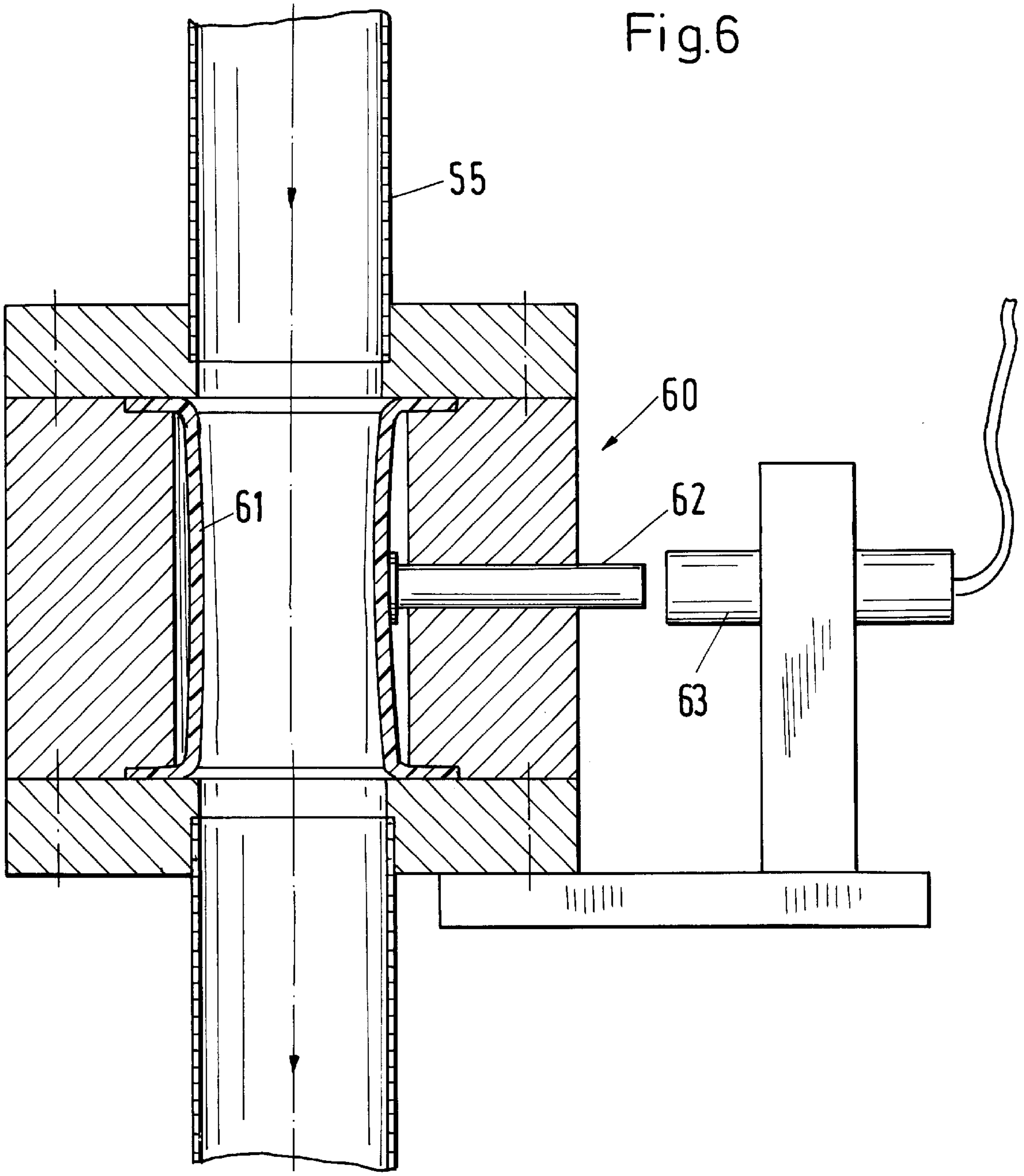
FIG. 6 shows a truncated presentation of a detail of the drying agent feeding pipe with control sensor.

Sensors 60 for checking the action of drying medium on the feed pipes 55, 59, are provided in the feed pipes 55, 57 as is illustrated for a feed pipe 55 in FIG. 6. Such sensors can have any suitable known construction. Preferably, however, they consist of a flexible sleeve 61, which forms an outer part of the outer boundary of the respective feed pipe 55, 57, expands when acted upon with drying medium on the inside and activates over a push rod 62 a control switch which, when not actuated, causes an error message to be displayed. By means of this control, it is ensured that each bottle receives the same treatment.

In the spray equipment 18, the sterilizing agent can be sprayed in with the help of a spray nozzle, as indicated in FIGS. 2 and 4. Instead of this, it is also possible to wet the interior of the bottles with a mist of sterilizing agent, hydrogen peroxide preferably being used as sterilizing agent. The sterilizing action is particularly advantageous here and is based on the fact that the mist of sterilizing agent can be applied specifically on the whole inner surface of the bottle in a finely dispersed form.

Figure 7:
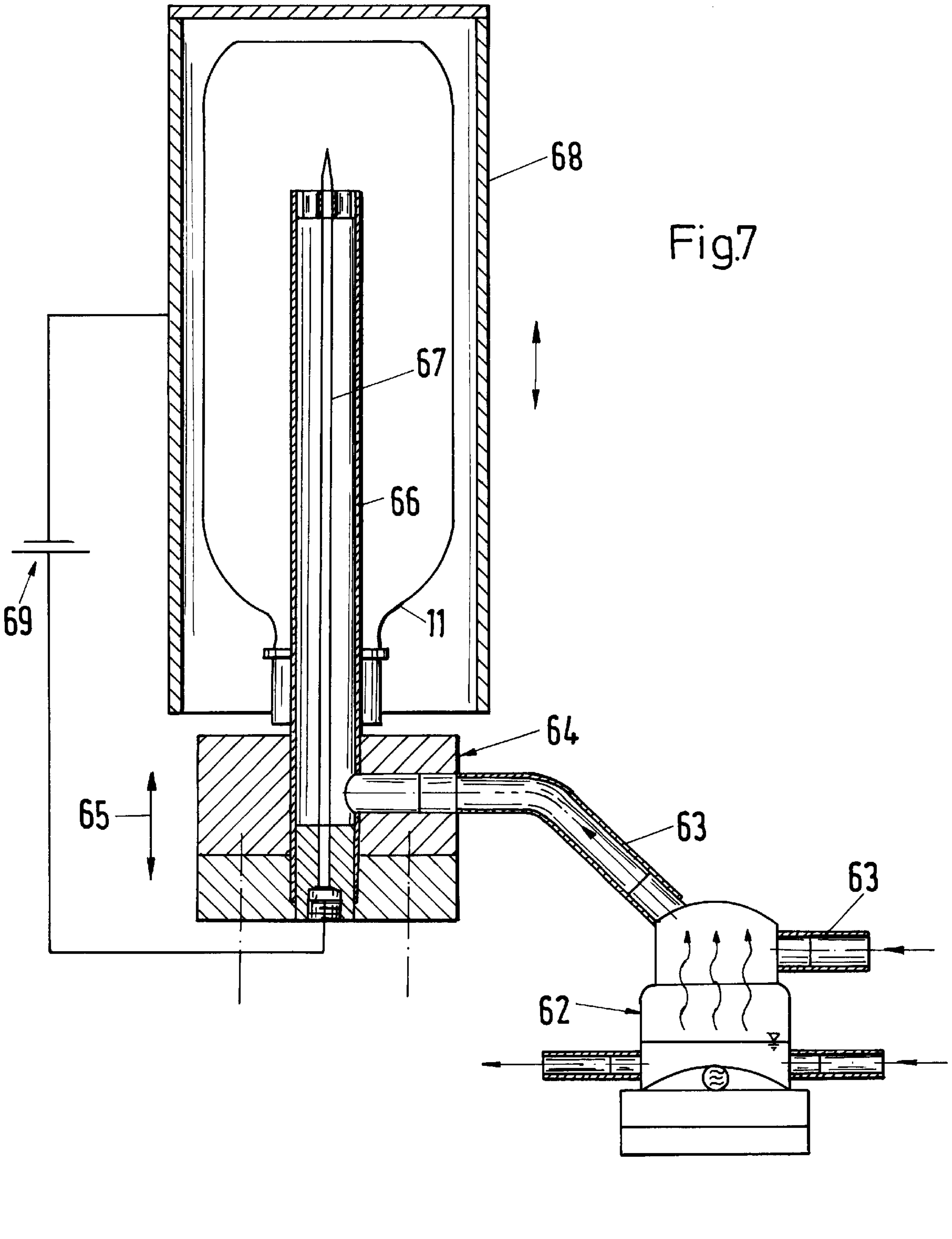
FIG. 7 shows a diagrammatic representation, partially sectional, of a sterilizing agent injector.

As is illustrated in greater detail in FIG. 7, a mist of sterilizing agent is generated by an ultrasonic generator 62 and fed into a stream of sterile air, which is supplied by the source 23 of sterile air, carried in a pipe 63, and generated in phase with the spraying equipment 18 and conveys the mist of sterilizing agent into the interior of the bottles 11 in the spraying equipment 18. The introduction of the mist of sterilizing agent into the interior of the bottles 11 takes place with the help of an injector 64, which can be moved by means of a lifting mechanism, the details of which are not shown, such as a pressure medium cylinder, in the direction of the arrows 65 vertically out of a lower starting position below the path of motion of the bottles 11 into the operating position, which is illustrated in FIG. 7 and in which its injection nozzles 66 engage the interior of each bottle 11 of a row of bottles in the sterilization position.

In each case, an electrically insulated, supported electrode 67 is assigned to the injection nozzles 66 and extends preferably coaxially through the nozzle pipe of the injection nozzles 66 and protrudes beyond this nozzle pipe some distance. Each electrode 67 interacts with a counter-electrode 68, which is assigned to the outside of the bottles 11 in the sterilization position, in order to build up an electrical field, which acts between the injection nozzle 66 and the wall of the bottles 11 and causes the mist droplets of sterilization agent, which are charged electrically by the electrode 67, to be moved selectively along the lines of force towards the interior wall of the bottles and to be deposited there. For generating this electric field, the electrode 67 and the counter-electrode 68 are connected to a source 69 of direct current.

As for the example illustrated in FIG. 7, the counter-electrode is constructed preferably as a cylindrical body, which in each case surrounds a bottle 11 at the outer periphery and at the bottom. By means of a driving mechanism that is not shown, such as a pressure medium cylinder, the counter-electrodes can be moved out of their lowered operating position shown vertically upwards into a starting position, in which they are outside of the path of motion of the bottles and permit the transverse row of bottles 11, which are to be sterilized, to be moved into the sterilization position.

After a transverse row of bottles 11, which are to be sterilized, has moved into the sterilization position, the counter-electrodes 68 are simultaneously lowered into the operating position shown and the injector 64 is raised out of its lower starting position into the also shown operating position, after which the electrical field is built up by connecting the two electrodes with the source 69 of direct current and, synchronously with the working cycle of the equipment, a flow of sterile air is generated in the pipe 63, which is connected to the source 23 of sterile air and conveys the mist of sterilizing agent into the interior of the bottle.

The ultrasonic generator 62, which generates the mist of sterilizing agent, can be connected over a closed-loop system 70 with the source 38 of sterilizing agent; however, it can also be connected with a (not shown) separate sterilization source on the advancing or receding side.

What is claimed is:

1. A method of preparing and filling open ended bottles with a product comprising the steps of:

disposing a plurality of said bottles in an upright disposition with the open end uppermost;

providing a conveyor for conveying the bottles along a conveying path;

loading a plurality of said upright bottles on said conveyor in a plurality of rows of bottles at a loading station along said conveying path with the longitudinal extent of each row being generally perpendicular to said conveying path;

inverting each row of upright bottles on said conveyor at an inverting station along said conveyor path to an inverted position in which the open ends of said bottles in each row are lowermost;

cleaning the inside of each inverted row of bottles at a cleaning station disposed along said conveying path;

drying each inverted row of bottles on said conveyor at a first drying station disposed along said conveying path;

providing a sterile enclosure along said conveying path;

sterilizing each inverted row of bottles on said conveyor with a sterilizing agent at a sterilizing station in said sterile enclosure;

drying the inside of each inverted row of bottles at a second drying station disposed in said sterile enclosure;

uprighting each row of bottles on said conveyor at an uprighting station disposed along said conveying path from said inverted position to said upright position while each row of bottles is in said sterile enclosure;

filling each row of upright bottles on said conveyor at a filling station with a product while each row of bottles is in said sterile enclosure;

sealing the open end of the row of filled bottles on said conveyor at a sealing station while each row of bottles is in said sterile enclosure; and unloading each row of sealed upright bottles from said conveyor at an unloading station.

2. A method according to claim 1, further comprising advancing said conveyor periodically to provide for simultaneously:

conveying each row of bottles from said loading station to said inverting station;

conveying each row of inverted bottles from said inverting station to said cleaning station;

conveying each row of inverted bottles from said cleaning station to said first drying station;

conveying each row of inverted bottles from said first drying station to the sterilizing station in the sterile enclosure;

conveying each row of inverted bottles from said sterilizing station to said second drying station;

conveying each row of inverted bottles from said second drying station to said uprighting station;

conveying each row of upright bottles from said uprighting station to said filling station;

conveying each row of upright and filled bottles from said filling station to said sealing station; and conveying each row of upright and sealed bottles from said sealing station to said unloading station.

3. A method according to claim 1, further comprising periodically stopping the conveyor, and substantially simultaneously performing said loading step, said inverting step, said cleaning step, said drying step at said first drying station, said sterilizing step, said drying step at said second drying station, said uprighting step, said filling step, said sealing step and said unloading step while said conveyor is stopped.

4. A method according to claim 1, wherein said inverting step, said cleaning step, said drying step at said first drying station, said sterilizing step, said drying step at said second drying station, said uprighting step, said filling step, and said sealing step are performed substantially simultaneously on each bottle in each row of bottles as said rows of bottle are progressively, sequentially, and discontinuously conveyed from said loading station to said unloading station.

5. A method according to claim 1, further comprising periodically stopping the conveyor to simultaneously dispose a row of bottles in each of said cleaning station, said first drying station, said sterilizing station, said second drying station, said filling station and said sealing station, substantially simultaneously performing said cleaning step on all of the bottles in the row of bottles stopped at said cleaning station, substantially simultaneously performing said drying step on all of the bottles in the row of bottles stopped at said first drying station, substantially simultaneously performing said sterilizing step on all of the bottles in the row of bottles stopped at said sterilizing station, substantially simultaneously performing said drying step on all of the bottles in the row of bottles stopped at said second drying station, substantially simultaneously performing said filling step on all of the bottles in the row of bottles stopped at said filling station, and substantially simultaneously performing said sealing step on all of the bottles in the row of bottles stopped at said sealing station.

6. A method according to claim 1, further comprising operating said conveyor over an endless closed loop.

7. A method according to claim 1, wherein said loading step includes disposing a plurality of said bottles in a bottle carrier which holds a row of said bottles, and operating said conveyor to convey said bottle carriers from said loading station to said unloading station.

8. A method according to claim 7, further comprising gripping said plurality of bottles in each row of bottles on each bottle carrier such that the relative spacing of each bottle in a row on each bottle carrier is maintained substantially unchanged as each bottle carrier is conveyed from said and loading station to said unloading station.

9. A method according to claim 1, further comprising gripping each bottle of said plurality of bottles in each row such as to retain each bottle in each row of bottles in said inverted disposition when each row of bottles is inverted to said inverted position at said inverting station.

10. A method according to claim 1, further comprising wetting the inside of each row of inverted bottles with sterile water within said sterile enclosure after said drying step at said second drying station.

11. A method according to claim 1, wherein said cleaning step at said cleaning station includes introducing into each row of bottles a liquid cleansing agent which is at a pressure of about 2 to 4 bar and a temperature of about 40° to 90° C.

12. A method according to claim 1, wherein said pressure is about 3 bar and said temperature is about 45° C.

13. A method according to claim 1, wherein said drying step at said first and second drying stations includes introducing into the rows of bottles a gaseous drying medium at a temperature of about 40° to 90° C. and under a pressure of about 2 to 4 bar.

14. A method according to claim 1, wherein said sterilizing step includes providing a mist of a sterilizing agent generated by ultrasound and injecting the mist of sterilizing agent into each row of bottles utilizing sterile air.

15. A method according to claim 1, wherein said sterilizing step includes including a heated and pressurized liquid sterilizing agent into each invented row bottles.

16. A method according to claim 15, wherein said liquid sterilizing agent is at a pressure of about 2 to 4 bar and a temperature of about 40° to 90° C.

17. Apparatus for preparing and filling open ended containers with a product in which the containers have an upright disposition in which the open ends are uppermost and an inverted disposition in which the open ends are lowermost comprising:

a conveyor for conveying the containers along a conveying path;

container carriers on said conveyor having an upright position and an inverted position;

a loading mechanism for loading a plurality of upright containers on said container carriers in a row at a loading station along said conveying path with the longitudinal extent of each row in each container carrier being generally perpendicular to said conveying path, said container carriers being disposed in an upright position at said loading station;

an inverting mechanism for inverting each container carrier on said conveyor at an inverting station along said conveying path from said upright position to an inverted position in which the upright containers in each container carrier are inverted to said inverted disposition;

a cleaning device for cleaning the inside of each inverted row of containers in each container carrier at a cleaning station disposed along said conveying path;

a first drying device for drying each inverted row of containers on each container carrier at a first drying station disposed along said conveying path;

a sterile enclosure disposed along said conveying path;

a sterilizing device for sterilizing each inverted row of containers on each container carrier with a sterilizing agent at a sterilizing station in said sterile enclosure;

a second drying device for drying the inside of each inverted row of containers on each container carrier at a second drying station disposed in said sterile enclosure;

an uprighting mechanism for uprighting each container carrier on said conveyor at an uprighting station along said conveying path from said inverted position to said upright position such that the containers in each container carrier are uprighted to said upright disposition while each row of containers is in said sterile enclosure;

a filling mechanism for filling each row of upright containers on each container carrier at a filling station with a product while each row of containers is in said sterile enclosure;

a sealing mechanism for sealing the open end of the filled containers in each container carrier on said conveyor at a sealing station while each row of containers is in said sterile enclosure;

said conveyor being operable to convey each container carrier carrying a row of filled and sealed upright containers out of said sterile enclosure to an unloading station disposed along said conveying path; and an unloading mechanism for unloading each container carrier carrying a row of filled and sealed upright containers from said conveyor at said unloading station.

18. Apparatus according to claim 17, further comprising a wetting device for wetting the inside of the inverted row of containers on each container carrier within said sterile enclosure with sterile water after the inside of each row of inverted containers have been dried by said second drying device.

19. Apparatus according to claim 17, wherein said conveyor includes endless chains disposed to traverse an endless loop, said container carriers being mounted on said endless chains at substantially equally spaced distances from one another, said container carriers being pivotal mounted on said endless chains for pivotal movement between said upright and inverted positions.

20. Apparatus according to claim 17, wherein each of said container carriers includes container holders for holding each container in each row of containers on each container carrier as said container carriers move from said loading mechanism to said unloading mechanism.

21. Apparatus according to claim 17, wherein each of said container carriers includes holders for holding each container on its respective container carrier as said inverting mechanism inverts each container carrier from said upright position to said inverted position.

22. Apparatus according to claim 17, wherein said sterilizing device includes an ultrasonic generator for ultrasonically atomizing said sterilizing agent and a nozzle connected to a source of sterile air for injecting said atomized sterilizing agent into the interior of said containers.

23. Apparatus according to claim 22, wherein said sterilizing device includes an electrically insulated first electrode in said nozzle and a second electrode on the outside of each container being sterilized, said first and second electrodes providing an electric field which promotes the application of said atomized sterilizing agent on the interior surface of said containers.

24. Apparatus according to claim 23, wherein each nozzle is an elongated nozzle having an elongated central passage, each first electrode in each nozzle being an elongated rod electrode centrally disposed in the respective nozzle passageway, said nozzle and its respective first electrode being moveable to a first position in which said nozzle and its respective first electrode are disposed inside said container, said second electrode being moveable to a first position in which said second electrode is disposed about the outside of said container, said nozzle and its respective first electrode being in said first position when said second electrode is in said first position, said nozzle and its respective first electrode being moveable to a second position in which each nozzle and its respective first electrode are disposed externally of said container, said second electrode being moveable to a second position in which said second electrode is removed from being disposed about the outside of each respective container, said nozzle and its respect first electrode being in said second position when said second electrode is in said second position.

25. Apparatus according to claim 17, wherein said first drying device includes a plurality of nozzles including a separate nozzle for each container in the row of containers in said first drying station, said plurality of nozzles being moveable simultaneously between first and second positions, said nozzles when in said first position being disposed in each respective container, said nozzles when in said second position being disposed outside each respective container.

26. Apparatus according to claim 25, wherein each nozzle is an elongate nozzle having an elongated central passage and an elongated outer passage surrounding said central passage, supply conduits for supplying a drying medium to said central passage and to said outer passage, each container having a bottom opposite its respective open end and a sidewall extending between said bottom and said open end, said central passage having a discharge opening operable to direct said drying medium to said bottom of each respective container, each outer passage having discharge openings operable to direct said drying medium to the side wall of each respective container.

27. Apparatus according to claim 26, wherein each container has a generally central longitudinal axis which is substantially vertically disposed when each container in a row of containers is disposed at said first drying station, said discharge openings in each outer passage discharging said drying medium generally radially outwardly of said longitudinal axis and generally downwardly at an acute angle relative to said longitudinal axis.

28. Apparatus according to claim 27, wherein said first drying device includes first and second conduits for independently supplying a drying medium to said central passage and to said outer passage of each nozzle.

29. Apparatus according to claim 27, wherein said first drying device includes exhaust equipment disposed about the open end of each inverted container of a row of containers in said first drying station for conducting the drying medium exiting the open end of each container away from the open end of each container.

30. Apparatus according to claim 27, wherein said first drying device includes a drying medium guide disposed about the open end of each inverted container for guiding the drying medium exiting from the open end of each container and for limiting the escape of said exiting drying medium from around the open end of each container.

31. Apparatus according to claim 17, wherein said first drying device further includes a conduit for supplying a drying medium to each container in a row of containers at said first drying station, and a sensor in said conduit for sensing that the drying medium has passed through said conduit.

32. Apparatus according to claim 31, wherein said sensor includes a flexible sleeve which forms a part of the outer boundary of said conduit, said flexible sleeve expanding when acted upon by a drying medium passing through the inside of said sleeve, said sensor further including a central switch, said flexible sleeve actuating said central switch when said flexible sleeve expands.

33. Apparatus according to claim 17, wherein said second drying device includes a plurality of nozzles including a separate nozzle for each container in the row of containers in said second drying station, said plurality of nozzles being moveable simultaneously between first and second positions, said nozzles when in said first position being disposed in each respective container, said nozzles when in said second position being disposed outside each respective container.

34. Apparatus for preparing and filling open ended containers with a product in which the containers have an upright disposition in which the open ends are uppermost and an inverted disposition in which the open ends are lowermost comprising:

a conveyor for conveying the containers along a conveying path;

container carriers on said conveyor having an upright position and an inverted position;

loading means for loading a plurality of upright containers on said container carriers in a row at a loading station with the longitudinal extent of each row in each container carrier being generally perpendicular to said conveying path, said container carriers being disposed in an upright position at said loading station;

inverting means for inverting each container carrier on said conveyor at an inverting station from said upright position to an inverted position in which the upright containers in each container carrier are inverted to said inverted disposition;

cleaning and drying means for cleaning and subsequently drying the inside of each inverted row of containers in each container carrier;

a sterile enclosure disposed along said conveying path;

sterilizing and drying means for sterilizing and subsequently drying each inverted row of containers on each container carrier in said sterile enclosure;

uprighting means for uprighting each container carrier on said conveyor at an uprighting station from said inverted position to said upright position such that the containers in each containers carrier are uprighted from said inverted disposition to said upright disposition while each row of containers is in said sterile enclosure;

filling and sealing means for filling and subsequently sealing each row of upright containers on each container carrier in said sterile enclosure; and unloading means for unloading each container carrier carrying a row of filled and sealed upright containers from said conveyor.

* * * * *

UNITED STATES PATENT AND TRADEMARK OFFICE

CERTIFICATE OF CORRECTION

PATENT NO. : 6,328,928 B1
DATED : December 11, 2001
INVENTOR(S) : Klaus Schroeder et al.

It is certified that error appears in the above-identified patent and that said Letters Patent is hereby corrected as shown below:

Title page,
Item [54], Title, this is a request for a Certificate of Correction to correct the Title of this Patent. Please correct the Title as follows: "METHOD AND FOR PREPARING CONTAINER FOR FILLING, AND METHOD OR FILLING CONTAINER"
to
-- METHOD AND APPARATUS FOR PREPARING CONTAINERS FOR FILLING, AND METHOD OF FILLING CONTAINERS --.

In addition, the U.S. National Stage of PCT application information was not inserted by the U.S. Patent Office in this Patent. Please insert the U.S. National Stage of PCT application information as follows:

| | | |
|---|---|---|
| -- [22] | PCT Filed | : **January 5, 1998** -- |
| -- [86] | PCT No. | : PCT/EP98/00028 |
| | § 371 Date | : March 3, 1999 |
| | § 102 (e) | : March 3, 1999 |
| -- [87] | PCT Pub. No. | : WO 98/30491-- |
| | PCT Pub. Date | : July 16, 1998 -- |

Signed and Sealed this

Thirteenth Day of August, 2002

*Attest:*

JAMES E. ROGAN

*Attesting Officer*

*Director of the United States Patent and Trademark Office*